United States Patent [19]

Ades et al.

[11] Patent Number: 4,522,750

[45] Date of Patent: Jun. 11, 1985

[54] CYTOTOXIC COMPOSITIONS OF TRANSFERRIN COUPLED TO VINCA ALKALOIDS

[75] Inventors: Edwin W. Ades, Indianapolis; George J. Cullinan, Trafalgar, both of Ind.

[73] Assignee: Eli Lilly and Company, Indianapolis, Ind.

[21] Appl. No.: 581,925

[22] Filed: Feb. 21, 1984

[51] Int. Cl.$^3$ .......................... C07G 7/00; C07G 7/04
[52] U.S. Cl. ................................ 260/112 R; 260/121
[58] Field of Search ............................ 260/112 R, 121

[56] References Cited

U.S. PATENT DOCUMENTS

| | | | |
|---|---|---|---|
| 3,392,173 | 7/1968 | Hargrove | 424/262 X |
| 3,959,249 | 5/1976 | Antonini | 260/121 X |
| 4,203,898 | 5/1980 | Cullinan et al. | 424/262 X |
| 4,434,156 | 2/1984 | Trowbridge | 424/85 |

OTHER PUBLICATIONS

Merck Index, 9th Ed. (1976), pp. 30, 896 and 1230.
J. Med. Chem., 22, 391–400 (1979), Conrad et al.
Basala, M. and Raso, V., Federation Proceedings, vol. 42, No. 3, Abstract 2289, p. 683 (1983).
Hopkins, C. R. and Trowbridge, I. S., J. Cell Biol., 97, 508–521 (1983).
Gatter, K. C., Brown, G., Strowbridge, I. S., Woolston, R-E and Mason, D. Y., J. Clin. Pathol., 36, 539–545 (1983).
MacGillivray, R. T. A., Mendex, E., Shewale, J. G., Sinha, S. K., Lineback–Zins, J. and Brew, K., J. Biol. Chem., 258, 3543–3553 (1983).
Johnson, J. R., Ford, C. H. J., Newman, C. E., Woodhouse, C. S., Rowland, G. F. and Simmonds, R. G. Br. J. Cancer, 44, 472–475 (1981).

*Primary Examiner*—Howard E. Schain
*Attorney, Agent, or Firm*—William C. Martens, Jr.; Arthur R. Whale

[57] ABSTRACT

There is provided by this invention cell-targeting cytotoxic compositions comprising transferrin covalently coupled to vinca alkaloid.

10 Claims, No Drawings

CYTOTOXIC COMPOSITIONS OF TRANSFERRIN COUPLED TO VINCA ALKALOIDS

BACKGROUND OF THE INVENTION

Attempts have been made over the past several years to use antibodies in covalent combination with cytotoxic agents, thereby seeking to effect selective action on target cells and to prevent or at least to substantially diminish the otherwise relatively nonspecific effect of cytotoxic agents. A review of the use of antibody-linked cytotoxic agents is provided in Ghose et al., J. Natl. Cancer. Inst. 61, 657–676 (1978).

Although much effort has been directed to the use of antibodies for cell-directing purposes, especially in view of the now available monoclonal antibodies, the search continues to discover other viable cell-directing moieties. It is to compositions containing one such cell-directing moiety that the present invention is directed.

Transferrin is a circulating glycoprotein that acts as a carrier for iron and therefore provides a mechanism for delivering iron to the hematopoietic system. Transferrin introduces iron into cells via transferrin receptors present on the cell surfaces. The number of transferrin receptors on the cell surface is dependent upon cell type and is highly variable. In general, however, those cells that domonstrate high proliferation tend correspondingly to have great numbers of transferrin receptors. One general class of cells having large numbers of transferrin receptors is tumor cells and, in particular, leukemia cells.

It is on the above premise that the present invention is founded.

SUMMARY OF THE INVENTION

Thus, the present invention is directed to a cell-targeting composition comprising transferrin covalently coupled to vinca alkaloid.

DETAILED DESCRIPTION OF THE INVENTION

One of the essential components of the compositions of this invention is a vinca alkaloid. Alkaloids obtainable from *Vinca rosea* represents a most productive source for drugs that adversely affect the growth of experimental malignancies in mammals. Initially, only selected alkaloids, available from leaves of the vinca plant by extraction and purifiable by chromatography, were found to be active. Included among these active antineoplastic alkaloids obtained directly from the vinca plant are VLB (vinblastine, vincaleucoblastine), vincristine (leurocrystine), leurosine (vinleurosine), leurosidine (vinrosidine), leuroformine (formylleurosine), and deoxy VLB "A" and "B" (4'-deoxy VLB and 4'-deoxyleurosidine).

Although the foregoing represent naturally-occurring isolatable antineoplastic agents, other active agents can be prepared by chemical modification of the isolated alkaloids. Chemical modification of the indole-dihydroindole alkaloids obtained from *Vinca rosea* generally has centered upon three areas of the molecule: C-3, C-4', and C-4.

With respect first to C-3 modifications, some of the more recent, and more successful, modifications of the basic indole-dihydroindole structure have been the C-3 carboxamide and C-3 carboxyhydrazide derivatives, most of which have been shown to be active anti-tumor agents [See U.S. Pat. No. 4,166,810, and Conrad et al., J. Med. Chem. 22, 391 (1979)]. 4-Desacetyl VLB 3-carboxamide (vindesine) is currently being marketed in several European countries as an oncolytic agent. It is effective in treating certain vincristine-resistant leukemias in addition to many common neoplasms, including germ-cell tumors. Reaction of the 3-hydroxy or 3-ester function with an isocyanate has produced corresponding oxazolidinedione derivatives. One of these, the N-chloroethyl derivative (vinzolidine), is currently undergoing clinical trial. These oxazolidinedione derivatives are disclosed in Miller and Gutowski, U.S. Pat. No. RE 30,560, reissued Mar. 31, 1981.

A second portion of the indole-dihydroindole molecule that has been modified is at C-4'. A majority of these modifications have been based on the 3',4'-anhydro derivative, which can be prepared either by coupling vindoline and catharanthine via a modified Polonovski reaction [Potier et al., J.C.S. Chem. Comm., 670 (1975)], or by dehydrating VLB or leurosidine (Gutowski and Miller, U.S. Pat. No. 4,029,663). The dehydration reaction produces two exo double bond isomers in addition to the delta 3',4'-anhydro derivative. Functionalization of any of these double bonds to form epoxides, diols, and the like, has been the basis of chemical modification at C-4'.

The third region of the indole-dihydroindole which has been successfully modified is C-4. First, hydrolysis of the acetoxy group, present in nearly all of the above vinca alkaloids, yields active antineoplastic 4-desacetyl derivatives. Vindesine, for example, referred to hereinabove as a C-3 carboxamide, is a 4-desacetyl derivative. Secondly, Hargrove (U.S. Pat. Nos. 3,387,001 and 3,392,173) prepared novel 4-acyl derivatives of 4-desacetyl VLB, 4-desacetyl vincristine, and the like. Among these new derivatives is 4-chloroacetyl VLB, which can be reacted with amines, for example, dimethylamine, to yield a potent anticancer drug, vinglycinate, N,N-dimethyl 4-glycinyl VLB. In a different modification, Wright and Neuss (U.S. Pat. No. 4,122,082), oxidized the 4-hydroxyl of 4-desacetyl VLB to the corresponding 4-keto compound. Thompson (U.S. Pat. No. 4,195,022) reduced the ketone to its 4-epihydroxy (4α-hydroxy) derivative, a compound having anticancer activity.

Using the foregoing as a foundation for defining the vinca alkaloids contemplated for use in the compositions of this invention, the following structural formula depicts generally the intended 4-desacetyl indole-dihydroindole alkaloids that may be used as starting materials:

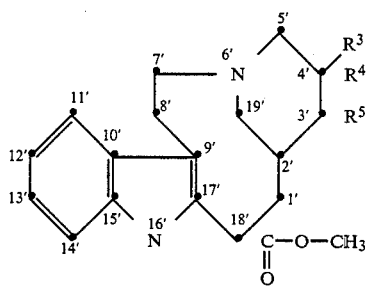

-continued

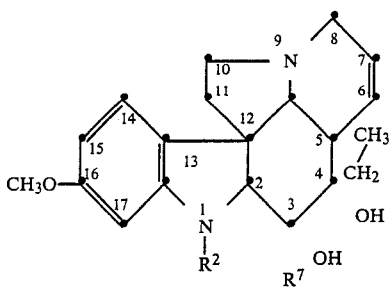

In the foregoing, $R^2$ is hydrogen, methyl, or formyl; $R^3$, $R^4$, and $R^5$ are interrelated such that (a) when $R^5$ is hydrogen, one of $R^3$ and $R^4$ is ethyl and the other is hydrogen or hydroxyl, and (b) when $R^4$ and $R^5$ are taken together with the carbons to which they are attached, they form an epoxide, and $R^3$ is ethyl; and $R^7$ is —COOH, —COOR$^8$, or —COR$^9$, in which $R^8$ is $C_1$-$C_3$ alkyl and $R^9$ is —NH$_2$, —NHR$^8$, —NHCH$_2$CH$_2$Cl, —NHCH$_2$CH$_2$YCH$_3$ in which Y is sulfur or oxygen, 1-pyrrolidyl, or 1-piperidinyl.

In the above formula, when $R^7$ is COOCH$_3$, $R^2$ is methyl, $R^3$ is hydroxyl, $R^4$ is ethyl, and $R^5$ is hydrogen, 4-desacetyl VLB (4-desacetyl vinblastine) is represented; when $R^7$ is COOCH$_3$, $R^2$ is formyl, $R^3$ is hydroxyl, $R^4$ is ethyl, and $R^5$ is hydrogen, 4-desacetyl vincristine is represented; when $R^7$ is COOCH$_3$, $R^2$ is methyl, $R^3$ is ethyl, $R^4$ is hydroxyl, and $R^5$ is hydrogen, 4-desacetyl leurosidine is represented; when $R^7$ is COOCH$_3$, $R^2$ is methyl or formyl, $R^3$ is ethyl, and $R^4$ and $R^5$ taken together with the carbons to which they are attached form an alpha-epoxide ring, 4-desacetyl leurosine and 4-desacetyl leuroformine, respectively, are represented; when $R^7$ is COOCH$_3$, $R^2$ is methyl, $R^3$ is ethyl, and $R^4$ and $R^5$ are hydrogen, 4-desacetyl deoxy VLB "B" (4-desacetyl-4'-deoxyleurosidine) is represented; when $R^7$ is COOCH$_3$, $R^2$ is methyl, $R^4$ is ethyl, and $R^3$ and $R^5$ are hydrogen, 4-desacetyl deoxy VLB "A" (4-desacetyl-4'-deoxy VLB) is represented; when $R^7$ is COOCH$_3$, $R^2$ is formyl, $R^3$ is ethyl, and $R^4$ and $R^5$ are hydrogen, 4-desacetyl-4'-epideoxyvincristine (4-desacetyl-1-formyl-1-desmethylleurosidine) is represented; and when $R^7$ is CONH$_2$, $R^2$ is methyl, $R^3$ is hydroxyl, $R^4$ is ethyl, and $R^5$ is hydrogen, vindesine (4-desacetyl-VLB 3-carboxamide) is represented. Other 3-carboxamide derivatives of the 4-desacetyl indole-dihydroindole alkaloids represented above are named accordingly; i.e., as the 3-(2-chloroethyl)carboxamide, as the 3-(2-methoxy)ethylcarboxamide, as the 3-(2-methylthio)ethylcarboxamide, as the 3-pyrrolidinyl derivative, as the N-methylcarboxamide derivative, and the like, for each of the amide groups comprehended within $R^7$ above. Compounds in which $R^7$ is a carboxyl "oic acids"; i.e., 4-desacetyl vinblastinoic acid, 4-desacetyl leurosinoic acid, 4-desacetyl vincristinoic acid, and the like. With regard to formation of derivatives of 4-desacetyl vinblastinoic acid, it will be appreciated by those skilled in the art that the 3-carboxyl must be protected with any of a number of routine carboxy protecting groups prior to reaction.

Literature references to the parent alkaloids of the 4-desacetyl derivatives are as follows: leurosine (U.S. Pat. No. 3,370,057), VLB (U.S. Pat. No. 3,097,137), leurosidine (vinrosidine) and leurocristine (vincristine) (U.S. Pat. No. 3,205,220), desmethyl VLB (U.S. Pat. No. 3,354,163), vindesine and other 3-carboxamides (U.S. Pat. No. 4,203,898), vinblastinoic acid and vincristinoic acid, (U.S. Pat. No. 4,012,390), 4'-epivincristine (U.S. Pat. No. 4,143,041) leuroformine and formylleurosine (U.S. Pat. No. 4,279,816), and deoxy VLB "A" and "B" [Tetrahedron Letters, 783 (1958)].

The second component of the composition of this invention is transferrin, preferably human transferrin. Transferrin is readily available commercially, e.g., from Sigma Chemical Company, St. Louis, Mo.

In the compositions of this invention, on the average, at least one molecule of a vinca alkaloid is present per molecule of transferrin such that the ratio on a molar basis generally ranges from about 1:1 to about 25:1, vinca alkaloid to transferrin. Preferably, the compositions contain an excess of vinca alkaloid, generally in an amount of from about 5 to about 20 moles of vinca alkaloid per mole of transferrin.

The two components of this invention, a vinca alkaloid and transferrin are coupled covalently via a linking agent. This covalent coupling is readily effected by modifying a 4-desacetyl indole-dihydroindole alkaloid, the structure of which is defined hereinbefore, to produce, through the 4-hydroxyl position, an entity having the formula $$R—O—CO—X—CO—Z \qquad (I)$$

in which R represents the 4-desacetyl indole-dihydroindole alkaloid moiety lacking the hydroxy in the 4-position.

In the foregoing formula, X is, for example, any of the following: $C_1$-$C_4$ alkylene, $C_2$-$C_4$ alkenylene, $C_2$-$C_4$ alkynylene, $C_3$-$C_6$ cycloalkylene, and phenylene. Preferably, X is $C_2$-alkylene(—CH$_2$—CH$_2$—), thereby defining a succinate moiety. Z defines a moiety which provides a point for transferrin coupling and is, for example, hydroxy, $C_1$-$C_3$ alkoxy, chloro, bromo, N$_3$, succinimidoxy, phthalimidoxy, benzotriazolyloxy, methanesulfonyloxy, tosyloxy, benzenesulfonyloxy, 2,2,2-trichloroethoxy, 2,2,2-tribromoethoxy, 2-iodoethoxy, benzyloxy, methylbenzyloxy, t-butyl, allylmethoxybenzyloxy, p-methoxybenzyloxy, p-nitrobenzyloxy, phenacyl, p-nitrophenacyl, p-methoxyphenacyl, p-methylphenacyl, diphenylmethyl, trityl, triphenylmethyl, trimethylacetyl, and the like.

In preparing compounds of the formula R—O—CO—X—CO—Z, a 4-desacetyl indole-dihydroindole, which can be prepared by the procedure of Hargrove, U.S. Pat. No. 3,392,173, is acylated with a carboxylic acid anhydride of the formula

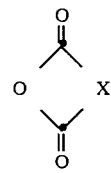

in which X is as herein defined, to yield a compound of formula I in which Z is hydroxyl. Compounds in which Z is —O—($C_1$-$C_3$ alkyl) are prepared from the half-acid, R—O—CO—X—COOH, via recognized esterification procedures using a $C_1$-$C_3$ alkanol. Methanol is the preferred alkanol.

Alternatively, compounds of the formula

R—O—CO—X—CO—O—(C$_1$-C$_3$ alkyl)

can be prepared directly by using a half ester, half acid chloride as the acylating agent; i.e., Cl—CO—X—CO—O—(C$_1$-C$_3$ alkyl). Other acylating groups can be used in place of Cl, and the acylating moiety can be represented generally by the formula Z$^1$—CO—X—CO—O—(C$_1$-C$_3$ alkyl)

in which X is as herein defined and Z$^1$ is Cl, Br, N$_3$, succinimidoxy, phthalimidoxy, methanesulfonyloxy, tosyloxy, phenylsulfonyloxy, benzotriazolyloxy, or other acylating moiety, Alternatively, an acylating agent of the formula Z$^1$—CO—X—CO—Z$^2$, in which Z$^2$ is a carboxy protecting group, can be used and the carboxy protecting group removed to yield a compound of the formula R—O—CO—X—COOH.

Alternative procedures for preparing several of the compounds of formula I involve the use of a coupling agent such as N,N-dicyclohexylcarbodiimide (DCC), N-ethoxycarbonyl-2-ethoxy-1,2-dihydroquinoline (EEDQ), and the like, under anhydrous reaction conditions with a half-acid of the formula H—CO—X—CO—Z$^2$ in which Z$^2$ is a carboxy protecting group. For example, an initial 4-succinoxy derivative can be prepared from a 4-desacetyl indole-dihydroindole and HO—CO—CH$_2$—CH$_2$—CO—Z$^2$ in the presence of DCC to yield a compound of the formula

R—O—CO—X—CO—Z$^2$.

Removal of the carboxy protecting group leads to a compound of formula I in which Z is hydroxyl.

Other intermediates are available by reaction of the compounds in which Z is hydroxyl, for example, with hydroxyphthalimide, hydroxybenzotriazole, and hydroxysuccinimide, to yield the corresponding products in which Z is, respectively, phthalimidooxy, benzotriazolyloxy, and succinimidooxy.

The compositions of this invention preferably are prepared using routine methods employed in peptide bond synthesis. Thus, for example, a compound of the formula R—O—CO—X—CO—Z in which Z is hydroxyl can be activated with N-methylmorpholine and isobutyl chloroformate. The activated molecule is converted, for example, to the corresponding succinimidooxy compound by reaction with N-hydroxysuccinimide. The resulting reactive intermediate then is treated with transferrin to produce the composition of this invention.

The compositions of this invention have general applicability to the specific and selective killing of cell types having transferrin receptors. As such, they are useful, for example, in the immunotherapy of cancer, and, in particular, leukemia, since such cells have an abundance of transferrin receptors. Moreover, the compositions of this invention have in vitro applications, including, for example, elimination of leukemic cells in bone marrow prior to autologous bone marrow transplantation.

The compositions of this invention can be used in a variety of pharmaceutical compositions and formulations and can be administered by a variety of conventional routes, such as intramuscular, intravenous, subcutaneous, and intraperitoneal.

In administering the compositions of this invention parenterally or intraperitoneally, the pharmaceutical forms suitable for injection include sterile aqueous solutions or dispersions and sterile powders for reconstitution into sterile injectible solutions or dispersions. The carrier can be a solvent or dispersing medium containing, for example, water, ethanol, polyol (for example glycerol, propylene glycol, liquid polyethyl glycol, and the like), suitable mixtures thereof, and vegetable oils. Proper fluidity can be maintained, for example, by the use of a coating such as lecithin, by the maintenance of the required particle size in the case of dispersion and by the use of surfactants. Prevention of the action of microorganisms can be ensured by various antibacterial and antifugal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin.

Sterile injectable solutions can be prepared by incorporating the compositions of this invention in the required amount of the appropriate solvent with various of the other ingredients, as desired.

If desired, and for more effective distribution, the compositions can be incorporated into slow release systems such as polymer matrices, liposomes, and microspheres. Moreover, the compositions of this invention can be administered either alone or as a mixture of a plurality of active ingredients.

Doses of the compositions of this invention are administered to the recipient for a period during which a therapeutic response is desired. The weight of the recipient and mode of administration will have an influence upon the size of the dose necessary to induce a particular response.

It is especially advantageous to formulate the compositions of this invention in unit dosage form for ease of administration and uniformity of dosage. Unit dosage form as used herein refers to a physically discrete unit suited as unitary dosages for the subject to be treated. Each unit contains a predetermined quantity of the composition calculated to produce the desired therapeutic effect in association with the pharmaceutically acceptable carrier. The specific unit dosage form is dictated by and directly dependent upon (a) the unique characteristics of the particular composition and (b) the particular therapeutic effect to be achieved.

The following examples are illustrative of this invention. They are not intended to be limiting upon the scope thereof.

EXAMPLE 1

Preparation of a Conjugate of Human Transferrin and Vinblastine Succinate Monoester The 4-desacetylvinblastine monoester of succinic acid (300 mg) was dissolved in 6 ml of methylene chloride, and 50 μl of N-methylmorpholine (NMM) was added. The resulting mixture was stirred and cooled to 0° C. in an ice bath. Isobutyl chloroformate (50 μl) was added, and the resulting mixture was stirred at 0° C. for about 15 minutes. N-Hydroxysuccinimide (50 mg) was added, and the mixture was warmed in a hot water bath for about 20 minutes. The reaction mixture then was evaporated to a tan residue.

One gram of human transferrin was dissolved in about 20 ml of water. The vinca-containing residue was dissolved in about 3 ml of dioxane, and the resultant solution was added to the transferrin solution. The pH of the transferrin solution (about 8.5) was lowered to about 6.5 by addition of the vinca solution, and the mixture became cloudy. The reaction mixture was stirred, and the pH was adjusted to 9.0 by addition of 0.5N sodium hydroxide after which about 10 ml of water were added. The mixture became clear upon stirring for about 20 minutes. Stirring was continued at room temperature for about 2 hours (final pH 7.4).

The mixture then was transferred to a dialysis bag having a molecular weight cut-off of about 12,000–14,000. Dialysis was continued with cooling against 1 liter of deionized water for 9 days with daily replacement of the water. The product was recovered by freeze drying to obtain 750 mg of the conjugate having an average ratio on a mole basis of about 20 vinca moieties per transferrin moiety.

EXAMPLE 2

Preparation of a Conjugate of Human Transferrin and Vindesine Succinate Monoester Human transferrin (100 mg) was dissolved in 13 ml of 0.34M borate buffer. The resulting mixture had a pH of 8.6. 4-Succinyl vindesine, activated by reaction with N-hydroxysuccinimide (12.4 mg), was dissolved in 0.2 ml of dry N,N-dimethylformamide, and the mixture was added to the stirring solution of human transferrin. The resulting mixture became cloudy with little or no pH change. The pH was lowered to about 6.0 by addition of 0.1N HCl, and a clear solution developed. The mixture then was stirred at room temperature for about 2 hours (final pH 6.1). The slightly cloudy mixture was placed in a dialysis bag (12,000–14,000 MW cut-off). Dialysis against 500 ml of deionized water with refrigeration was carried out for about 7 days with daily changing of the water. The mixture then was freeze-dried to obtain 67 mg of the conjugate.

Biological Activity

A vinca-transferrin conjugate was tested for activity against the P1534J lymphocytic leukemia (solid form). This solid leukemia was obtained in 1973 from the Jackson Laboratory (Bar Harbor, Maine). Tumor was removed from passage animals and minced into 1–3 mm. square fragments using sterile techniques. Tumor pieces were checked for sterility using both Antibiotic Medium 1 and Brain Heart Infusion (Difco; Detroit, Mich.). Recipient mice were shaved, and tumor pieces were implanted subcutaneously in the axillary region by tracar. A single dose of the test compound in saline was administered intravenously on the day following tumor implant. Food and water were provided ad libitum. All animals were weighed at the beginning and end of the test period. On days 10 to 12, two dimensional measurements (width and length) of all tumors were taken using vernier calipers. Tumor weights were calculated from these measurements using the following formula:

$$\text{Tumor Weight (mg)} = \frac{\text{Tumor Length (mm)} \times \text{Tumor Width (mm)}^2}{2}$$

Compounds are considered active if more than 25% inhibition of tumor growth is achieved at maximally tolerated doses. Results are provided in the Table following.

TABLE

Antitumor Test

| Test Compound[1] | Dose, (mg/kg) | Toxic, Total | Ave. Tumor Wt., (mg. ± St. Dev.) | Inhibition, Percent |
|---|---|---|---|---|
| Control (saline) | | 0/20 | 9807 ± 2303 | |
| A | 144.00 | 0/10 | 3958 ± 2037 | 60 |
| " | 72.00 | 0/10 | 7912 ± 1077 | 19 |
| " | 36.00 | 0/10 | 9497 ± 1824 | 3 |
| " | 18.00 | 0/10 | 11592 ± 2143 | 0 |
| B | 12.00 | 9/10 | 0 | 100 |
| " | 6.00 | 4/10 | 1553 ± 691 | 84 |
| " | 3.00 | 0/10 | 2175 ± 1171 | 78 |
| C | 3.00 | 3/10 | 907 ± 513 | 91 |
| " | 1.50 | 1/10 | 2196 ± 824 | 78 |
| " | .75 | 1/10 | 3482 ± 1087 | 64 |
| D | 72.00 | 10/10 | TOXIC | — |
| " | 36.00 | 4/10 | 918 ± 560 | 91 |
| " | 18.00 | 2/10 | 4255 ± 944 | 57 |

Test compounds are:
A. Conjugate of human transferrin and 4-desacetylvinblastine monoester of succinic acid (approximate mole ratio of 20:1, vinca:transferrin)
B. Vinblastine
C. 4-Desacetylvinblastine
D. 4-Desacetylvinblastine monoester of succinic acid

We claim:
1. A cell-targeting composition comprising transferrin covalently coupled to vinca alkaloid.
2. Composition of claim 1, in which the ratio, on a molar basis, vinca alkaloid to transferrin, is from about 1:1 to about 25:1.
3. Composition of claim 1, in which the ratio, an a molar basis, vinca alkaloid to transferrin, is from about 5:1 to about 20:1.
4. Composition of claim 3, in which the transferrin is human transferrin.
5. Composition of claim 4, in which the vinca alkaloid is vinblastine.
6. Composition of claim 5, in which transferrin is coupled to vinblastine via a succinate linkage.
7. Composition of claim 4, in which the vinca alkaloid is vindesine.
8. Composition of claim 7, in which transferrin is coupled to vindesine via a succinate linkage.
9. Composition of claim 4, in which the vinca alkaloid is vincristine.
10. Composition of claim 9, in which transferrin is coupled to vincristine via a succinate linkage.

* * * * *

Notice of Adverse Decisions in Interference

In Interference No. 102,657 involving Patent No. 4,522,750, E. W. Ades, G. J. Cullinan, CYTOTOXIC COMPOSITIONS OF TRANSFERRIN COUPLED TO VINCA ALKALOIDS, final judgment adverse to the patentees was rendered Oct. 31, 1991, as to claims 1-10.
*(Official Gazette December 24, 1991)*